(12) United States Patent
Castaneda et al.

(10) Patent No.: US 8,834,537 B2
(45) Date of Patent: *Sep. 16, 2014

(54) DRILL GUIDES FOR BONE PLATE

(71) Applicant: Biomet C.V., Gibraltar (GI)

(72) Inventors: Javier E. Castaneda, Miami, FL (US); Jorge L. Orbay, Coral Gables, FL (US); William F. Doyle, New York, NY (US); Robert Graham, Miami, FL (US)

(73) Assignee: Biomet C.V., Gibraltar (GI)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,725

(22) Filed: Jun. 10, 2013

(65) Prior Publication Data

US 2014/0039560 A1    Feb. 6, 2014

Related U.S. Application Data

(63) Continuation of application No. 12/977,705, filed on Dec. 23, 2010, which is a continuation of application No. 11/011,917, filed on Dec. 14, 2004, now Pat. No. 8,172,886.

(51) Int. Cl.
| | |
|---|---|
| *A61B 17/58* | (2006.01) |
| *A61B 17/80* | (2006.01) |
| *A61B 17/88* | (2006.01) |
| *A61B 19/00* | (2006.01) |
| *A61B 17/17* | (2006.01) |

(52) U.S. Cl.
CPC ......... *A61B 17/1728* (2013.01); *A61B 17/888* (2013.01); *A61B 2019/444* (2013.01); *A61B 2017/1782* (2013.01); *A61B 17/80* (2013.01); *A61B 2019/462* (2013.01); *A61B 17/8888* (2013.01)

USPC ............ 606/291; 606/280; 606/86 B; 606/96

(58) Field of Classification Search
USPC ........... 606/280–301, 70, 71, 305, 104, 86 B, 606/86 R, 96–98; 408/72 B, 115 B, 202, 204, 408/241 B, 241 G; 433/72–76, 215
See application file for complete search history.

(56) References Cited

U.S. PATENT DOCUMENTS

| | | | |
|---|---|---|---|
| 1,105,105 | A | 7/1914 | Sherman |
| 1,326,907 | A | 1/1920 | Bond |

(Continued)

FOREIGN PATENT DOCUMENTS

| | | |
|---|---|---|
| AU | 20027914 | 3/2001 |
| CH | 373516 | 11/1963 |

(Continued)

OTHER PUBLICATIONS

The Titanium Distal Radius Plate Technique Guide; Synthes, 1996.

(Continued)

*Primary Examiner* — Jerry Cumberledge
*Assistant Examiner* — Tara Carter
(74) *Attorney, Agent, or Firm* — Gordon & Jacobson, PC

(57) ABSTRACT

Removable drill guide tips are provided for simultaneous assembly relative to the holes of a bone plate. The drill guide tips may be used with an extension to together function as a conventional drill guide. After drilling, the extension or another tool is used to remove the tips from the plate. According to another use, the tip is used as a guide for a drill bit without any additional extension and then removed with a tool.

20 Claims, 5 Drawing Sheets

(56) References Cited

U.S. PATENT DOCUMENTS

| | | | |
|---|---|---|---|
| 2,406,832 A | 9/1946 | Hardinge | |
| 2,443,363 A | 6/1948 | Townsend et al. | |
| 2,494,229 A * | 1/1950 | Collison | 606/916 |
| 2,500,370 A | 3/1950 | McKibbin | |
| 3,289,290 A | 12/1966 | Sandor | |
| 3,673,378 A | 6/1972 | Kesling | |
| 3,713,221 A | 1/1973 | Malmin | |
| 3,741,205 A * | 6/1973 | Markolf et al. | 606/291 |
| 3,824,834 A | 7/1974 | Durham | |
| 3,842,825 A | 10/1974 | Wagner | |
| 3,874,808 A * | 4/1975 | Zaccardelli et al. | 408/1 R |
| 4,304,117 A | 12/1981 | Rawson | |
| 4,364,382 A | 12/1982 | Mennen | |
| 4,493,317 A | 1/1985 | Klaue | |
| 4,565,193 A | 1/1986 | Streli | |
| 4,683,878 A | 8/1987 | Carter | |
| 4,740,117 A | 4/1988 | Schaff Deleury et al. | |
| 4,867,144 A | 9/1989 | Karas et al. | |
| 4,889,110 A | 12/1989 | Galline et al. | |
| 4,905,680 A | 3/1990 | Tunc | |
| 4,955,886 A | 9/1990 | Pawluk | |
| 4,957,497 A | 9/1990 | Hoogland et al. | |
| 5,002,544 A | 3/1991 | Klaue et al. | |
| 5,015,248 A | 5/1991 | Burstein et al. | |
| 5,022,277 A | 6/1991 | Shaffer | |
| 5,053,036 A | 10/1991 | Perren et al. | |
| 5,139,497 A | 8/1992 | Tilghman et al. | |
| 5,151,103 A | 9/1992 | Tepic et al. | |
| 5,161,404 A | 11/1992 | Hayes | |
| 5,190,544 A | 3/1993 | Chapman et al. | |
| 5,197,966 A | 3/1993 | Sommerkamp | |
| 5,201,737 A | 4/1993 | Leibinger et al. | |
| 5,269,784 A | 12/1993 | Mast | |
| 5,290,288 A | 3/1994 | Vignaud et al. | |
| 5,304,180 A | 4/1994 | Slocum | |
| 5,336,224 A | 8/1994 | Selman | |
| 5,360,448 A | 11/1994 | Thramann | |
| 5,364,398 A | 11/1994 | Chapman et al. | |
| 5,366,326 A | 11/1994 | Converse | |
| 5,372,598 A | 12/1994 | Luhr et al. | |
| 5,413,577 A | 5/1995 | Pollock | |
| 5,423,826 A | 6/1995 | Coates et al. | |
| 5,474,553 A | 12/1995 | Baumgart | |
| 5,487,743 A | 1/1996 | Laurain et al. | |
| 5,507,801 A | 4/1996 | Gisin et al. | |
| 5,509,933 A | 4/1996 | Davidson et al. | |
| 5,558,674 A | 9/1996 | Heggeness et al. | |
| 5,564,302 A | 10/1996 | Watrous | |
| 5,578,036 A | 11/1996 | Stone et al. | |
| 5,586,985 A | 12/1996 | Putnam et al. | |
| 5,601,553 A | 2/1997 | Trebing et al. | |
| 5,634,927 A | 6/1997 | Houston et al. | |
| D383,841 S | 9/1997 | Runciman | |
| 5,693,055 A | 12/1997 | Zahiri et al. | |
| 5,718,705 A | 2/1998 | Sammarco | |
| 5,746,742 A | 5/1998 | Runciman et al. | |
| 5,752,958 A | 5/1998 | Wellisz | |
| 5,779,706 A | 7/1998 | Tschakaloff | |
| 5,785,712 A | 7/1998 | Runciman et al. | |
| 5,800,168 A | 9/1998 | Cascione et al. | |
| 5,807,396 A | 9/1998 | Raveh | |
| 5,851,207 A | 12/1998 | Cesarone | |
| 5,888,034 A | 3/1999 | Greenberg | |
| 5,935,128 A | 8/1999 | Carter et al. | |
| 5,954,722 A | 9/1999 | Bono | |
| 5,984,925 A | 11/1999 | Apgar | |
| 5,993,449 A | 11/1999 | Schlapfer et al. | |
| 6,001,099 A | 12/1999 | Huebner | |
| 6,007,535 A | 12/1999 | Rayhack et al. | |
| 6,066,142 A | 5/2000 | Serbousek et al. | |
| 6,077,271 A | 6/2000 | Huebner et al. | |
| 6,123,709 A | 9/2000 | Jones | |
| 6,129,730 A | 10/2000 | Bono et al. | |
| 6,162,243 A | 12/2000 | Gray et al. | |
| 6,162,253 A | 12/2000 | Conzemius et al. | |
| 6,170,803 B1 | 1/2001 | Liberfarb | |
| 6,193,721 B1 | 2/2001 | Michelson | |
| 6,235,034 B1 | 5/2001 | Bray | |
| 6,283,973 B1 | 9/2001 | Hubbard et al. | |
| 6,306,139 B1 | 10/2001 | Fuentes | |
| 6,306,171 B1 | 10/2001 | Conzemius | |
| 6,325,803 B1 | 12/2001 | Schumacher et al. | |
| 6,332,887 B1 | 12/2001 | Knox | |
| 6,348,052 B1 | 2/2002 | Sammarco | |
| 6,358,250 B1 | 3/2002 | Orbay | |
| 6,364,881 B1 | 4/2002 | Apgar et al. | |
| 6,364,882 B1 | 4/2002 | Orbay | |
| 6,416,518 B1 | 7/2002 | DeMayo | |
| 6,436,103 B1 | 8/2002 | Suddaby | |
| 6,506,191 B1 | 1/2003 | Joos | |
| 6,587,750 B2 | 7/2003 | Gerbi et al. | |
| 6,602,255 B1 | 8/2003 | Campbell et al. | |
| 6,623,486 B1 | 9/2003 | Weaver et al. | |
| 6,656,181 B2 | 12/2003 | Dixon et al. | |
| 6,663,632 B1 | 12/2003 | Frigg | |
| 6,695,845 B2 | 2/2004 | Dixon et al. | |
| 6,712,818 B1 | 3/2004 | Michelson | |
| 6,730,091 B1 | 5/2004 | Pfefferle et al. | |
| 6,821,278 B2 | 11/2004 | Frigg et al. | |
| 6,866,665 B2 | 3/2005 | Orbay | |
| 6,928,733 B2 | 8/2005 | Rubbert et al. | |
| 6,960,211 B1 | 11/2005 | Pfefferle et al. | |
| 7,048,477 B2 | 5/2006 | Abrams | |
| 7,128,744 B2 | 10/2006 | Weaver et al. | |
| 7,179,260 B2 | 2/2007 | Gerlach et al. | |
| 7,189,237 B2 | 3/2007 | Huebner | |
| 7,229,446 B2 | 6/2007 | Capanni | |
| 7,273,481 B2 | 9/2007 | Lombardo et al. | |
| 7,357,804 B2 | 4/2008 | Binder et al. | |
| 7,473,257 B2 | 1/2009 | Knopfle et al. | |
| 7,578,825 B2 | 8/2009 | Huebner | |
| 7,740,634 B2 | 6/2010 | Orbay et al. | |
| 7,771,433 B2 | 8/2010 | Orbay et al. | |
| 7,935,126 B2 | 5/2011 | Orbay et al. | |
| 8,172,886 B2 | 5/2012 | Castaneda et al. | |
| 8,241,338 B2 | 8/2012 | Castaneda et al. | |
| 8,545,540 B2 | 10/2013 | Orbay et al. | |
| 2001/0037156 A1 | 11/2001 | Burstein et al. | |
| 2002/0032446 A1 | 3/2002 | Orbay | |
| 2002/0042654 A1 | 4/2002 | Masini | |
| 2002/0045897 A1 | 4/2002 | Dixon et al. | |
| 2002/0156474 A1 | 10/2002 | Wack et al. | |
| 2003/0040753 A1 | 2/2003 | Daum et al. | |
| 2003/0083667 A1 | 5/2003 | Ralph et al. | |
| 2003/0171754 A1 | 9/2003 | Del Medico | |
| 2003/0225411 A1 | 12/2003 | Miller | |
| 2004/0034356 A1 | 2/2004 | LeHuec et al. | |
| 2004/0097937 A1 | 5/2004 | Pike et al. | |
| 2004/0102777 A1 | 5/2004 | Huebner | |
| 2004/0102778 A1 | 5/2004 | Huebner et al. | |
| 2004/0116930 A1 | 6/2004 | O'Driscoll et al. | |
| 2004/0186482 A1 | 9/2004 | Kolb et al. | |
| 2004/0219479 A1 | 11/2004 | Malin et al. | |
| 2005/0011659 A1 | 1/2005 | Tempelman et al. | |
| 2005/0028398 A1 | 2/2005 | Jacobsen | |
| 2005/0049594 A1 | 3/2005 | Wack et al. | |
| 2005/0049710 A1 | 3/2005 | O'Driscoll et al. | |
| 2005/0086939 A1 | 4/2005 | Schmid | |
| 2005/0090825 A1 | 4/2005 | Pfefferle et al. | |
| 2005/0101961 A1 | 5/2005 | Huebner et al. | |
| 2005/0165401 A1 | 7/2005 | Pack | |
| 2005/0182406 A1 | 8/2005 | Orbay et al. | |
| 2005/0187552 A1 | 8/2005 | Michelson | |
| 2005/0216090 A1 | 9/2005 | O'Driscoll et al. | |
| 2005/0234467 A1 * | 10/2005 | Rains | 606/96 |
| 2005/0261688 A1 | 11/2005 | Grady, Jr. et al. | |
| 2006/0089648 A1 | 4/2006 | Masini | |
| 2006/0149265 A1 | 7/2006 | James et al. | |
| 2006/0161158 A1 | 7/2006 | Orbay et al. | |
| 2006/0173459 A1 | 8/2006 | Kay et al. | |
| 2006/0195104 A1 | 8/2006 | Schlafli et al. | |
| 2006/0200145 A1 | 9/2006 | Kay et al. | |
| 2006/0264949 A1 | 11/2006 | Kohut et al. | |

(56) References Cited

U.S. PATENT DOCUMENTS

2007/0225714 A1 9/2007 Gradl
2007/0233111 A1 10/2007 Orbay et al.
2008/0009951 A1 1/2008 Hodge

FOREIGN PATENT DOCUMENTS

| DE | 19936061 | 3/2000 |
| --- | --- | --- |
| DE | 10015734 | 9/2001 |
| EP | 0471419 | 2/1992 |
| EP | 1836982 | 9/2007 |
| FR | 2367479 | 5/1978 |
| JP | 2003-102743 | 4/2003 |
| WO | WO99/05968 | 2/1999 |
| WO | WO01/91660 | 12/2001 |
| WO | WO03/007832 | 1/2003 |
| WO | WO2004/024009 | 3/2004 |
| WO | WO2004/045455 | 6/2004 |
| WO | WO2004/084701 | 10/2004 |
| WO | WO2005020851 | 3/2005 |
| WO | WO2005023127 | 3/2005 |
| WO | WO2006065512 | 6/2006 |

OTHER PUBLICATIONS

The Distal Radius Plate Instrument and Implant Set Technique Guide; Synthes, 1995.
SCS/V Distal Radius Plate Volar; Avanta; 1998.
SCS/D Distal Radius Plate System; Avanta; 1997.
Sumary of Safety and Effectiveness Information; Synthes (USA); 1998.
Hand Innovations, DVR Anatomic Plate with F.A.S.T. Guide Technology, DVR Anatomic The Proven Standard in Volar Plating, on sale as of Mar. 2005.
U.S. Appl. No. 12/977,705, filed Dec. 23, 2010, Applicant: Javier E. Castaneda et al.
U.S. Appl. No. 12/818,467, filed Jun. 18, 2010, Applicant: Jorge L. Orbay et al.
Graduated Stability Plates (GSP); Stryker Corporation; 2004.
U.S. Appl. No. 13/075,654, filed Mar. 30, 2011, Applicant: Jorge L. Orbay et al.

* cited by examiner

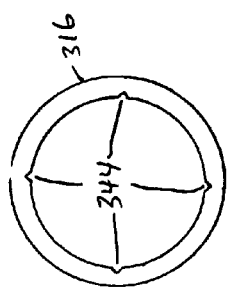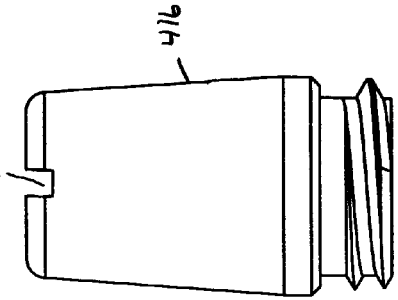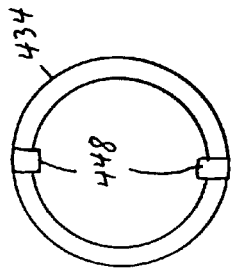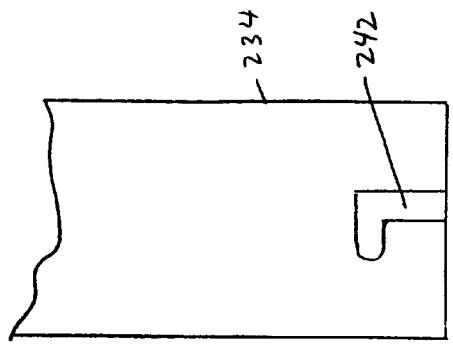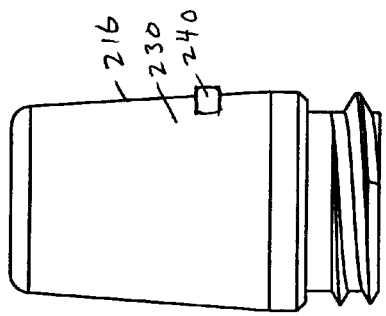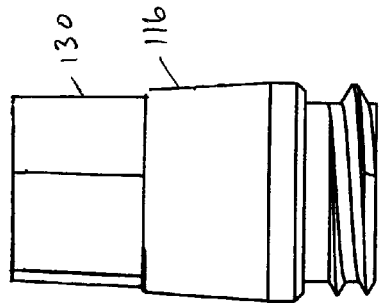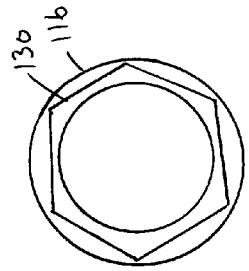

DRILL GUIDES FOR BONE PLATE

RELATED CASES

This application is a continuation of U.S. Ser. No. 12/977, 705, filed Dec. 23, 2010, which is a continuation of U.S. Ser. No. 11/011,917, filed Dec. 14, 2004, now issued as U.S. Pat. No. 8,172,886, which are hereby incorporated by reference herein in their entireties.

BACKGROUND OF THE INVENTION

1. Field of the Invention

This invention relates broadly to surgical devices. More particularly, this invention relates to orthopedic implants, and specifically to bone plates and drill guides.

2. State of the Art

Fracture to the metaphysis of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic.

Plating utilizes a stabilizing metal plate typically placed against the bone, fixed-angle pegs (which may have threaded or non-threaded shafts) positioned through the plate and entering drilled holes adjacent an articular bone surface, and cortical screws extending from the plate into holes drilled in the bone to provide stabilized fracture fixation. For example, co-owned U.S. Ser. No. 10/664,371, which is hereby incorporated by reference herein in its entirety, discloses a plate particularly adapted to treat dorsally displaced metaphyseal fractures from the volar side of the wrist.

When fixed-angle pegs are utilized in conjunction with a bone plate, it is necessary to ensure that the pilot holes drilled for the pegs are co-axial with the hole axes. Otherwise, the shaft of the pegs will not properly align with the anatomy, and the head of the pegs will not properly align with the threaded holes of the plate, potentially resulting in cross-threading. As a result, with the plate placed upon the bone, prior to drilling each hole in the bone in alignment with a peg hole, a drill guide is attached to the plate at the peg hole. The guide defines a tubular passage which directs the drill bit in the proper orientation for a peg through the particular peg hole. After drilling each hole, the drill guide is removed, the peg is inserted in the peg hole, and the drill guide is coupled to a subsequent peg hole.

The process of attaching the drill guide during the surgical procedure is laborious. It can be difficult to locate the appropriate angle for threadably coupling the guide to the peg hole during the procedure, given that each peg hole may have a discrete axis angle from the other peg holes. Such difficulty can unnecessarily prolong the surgical procedure.

SUMMARY OF THE INVENTION

It is therefore an object of the invention to provide facilitate the drilling of holes in bone in alignment with the peg holes in a bone plate.

It is another object of the invention to obviate the difficulties presented in connecting a drill guide in alignment with a hole in a bone plate at the time of surgery.

In accord with these objects, which will be discussed in detail below, drill guide tips are pre-assembled into at least one and preferably each of the threaded holes of the plate, so that surgeon does not have to thread the drill guide with the plate positioned on the bone. The pre-assembly can be done by the operating room technician or at the factory. The drill guide tips may be reusable or disposable. The tips are sufficiently short enough so that they do not interfere with adjacent tips or adjacent structure on the plate or intended to be inserted through the plate.

In a preferred method of pre-assembling the tips to the plate, a nest of short pins is placed beneath the plate such that the pins extend through the holes in the plate along the same angles as the axes of the holes. The pins then guide the tips to be thread into the holes at the correct angle. Alternatively, no nest is utilized and the tips are individually guided into the holes at the appropriate angle.

There are two options for using the tips. One is to attach a drill guide extension. The tip and extension together function as a conventional drill guide. After drilling, the extension is used to remove the tip from the plate. According to another use, the tip is used as a guide for a drill bit without any additional extension and then removed with a separate tool.

Additional objects and advantages of the invention will become apparent to those skilled in the art upon reference to the detailed description taken in conjunction with the provided figures.

BRIEF DESCRIPTION OF THE DRAWINGS

FIG. 6 is a side elevation of a first embodiment of a drill guide tip;

FIG. 7 is a top view of the first embodiment of the drill guide tip;

FIG. 8 is a side elevation of a second embodiment of a drill guide tip;

FIG. 9 is a side elevation view of an embodiment of drill guide extension;

FIG. 10 is a top view of a third embodiment of a drill guide tip;

FIG. 11 is a side elevation of a fourth embodiment of a drill guide tip; and

FIG. 12 is a bottom view of an embodiment of a drill guide extension engageable with the drill guide tip of FIG. 11.

DETAILED DESCRIPTION OF THE PREFERRED EMBODIMENTS

Figure 1:
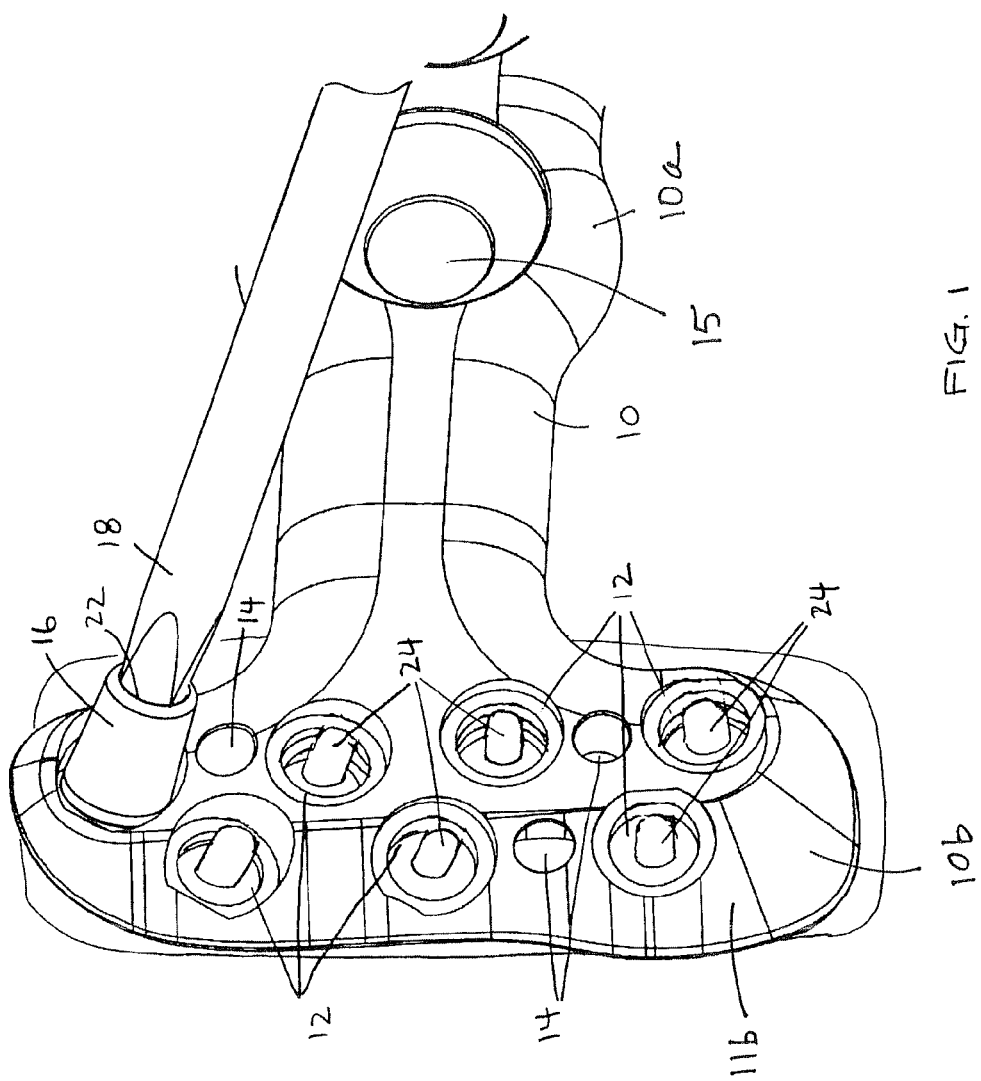
FIG. 1 is a perspective view of a bone plate and a drill guide tip being inserted or removed from the plate with a tool.
Figure 2:
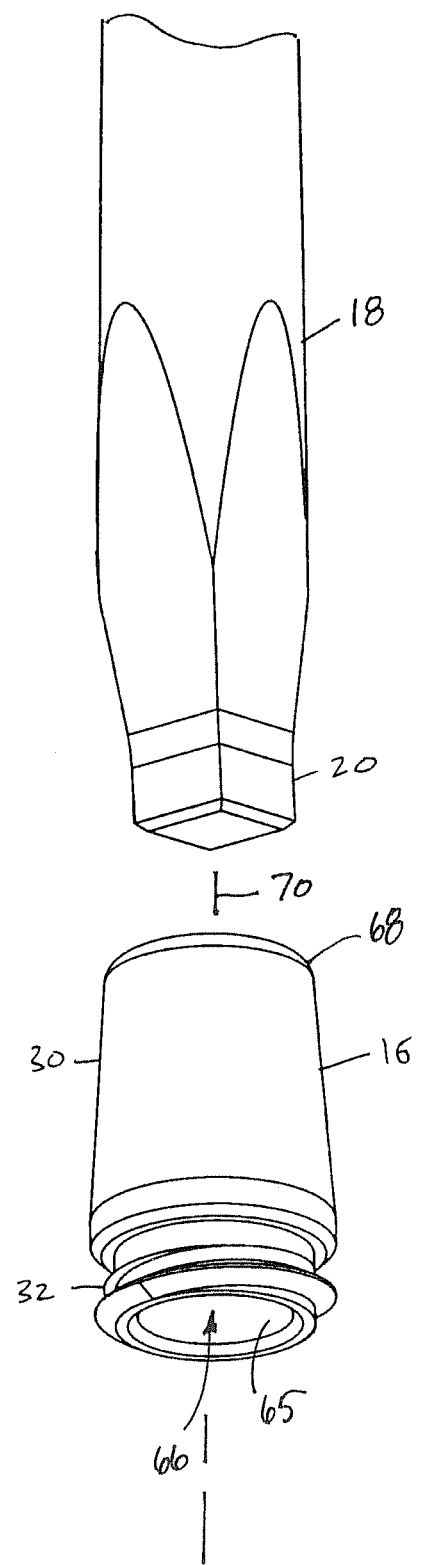
FIG. 2 is an exploded perspective view of drill guide tip and tool.

Turning now to FIG. 1, a bone plate 10 is shown. The bone plate shown is particularly for placement over the volar side of the distal radius and defines a shaft 10a for placement along the diaphysis of the distal radius bone and a head 10b angled out of lane relative to the shaft 10a (see FIG. 4) for placement at the metaphysis of the distal radius bone. The bone plate preferably has a thickness of 0.1 inch between a bone contacting first surface 11a and an opposed second surface 11b (FIGS. 1 and 4). The bone plate 10 includes a plurality of threaded peg holes 12 for threadably receiving the heads of pegs or locking screws (not shown) therein and relatively smaller alignment holes 14 adjacent the threaded holes sized to closely receive K-wires 50 in a fixed angle orientation (FIG. 3), and other relatively larger fastener holes 15 in the shaft 10a. The threaded peg holes 12 are separated into two sets arranged in proximal and distal rows which are displaced from each other longitudinally, with the longitudinally offset distal row located in a thinning distal region of the plate. In a preferred bone plate, the axes, e.g., axes 60, 62 (FIG. 3), of the peg holes are all oblique relative to each other. In one of the peg holes, a drill guide tip 16 is shown being pre-assembled into the hole with an insertion tool 18. Referring to FIGS. 1 and 2, in a preferred embodiment, the engagement between the insertion tool 18 and tip 16 is a tapered square 20 engaging a circular opening 22, with the edges of the square driver providing sufficient frictional force to rotate the tip into and out of engagement with the plate 10. Other suitable engagements may be used as well.

Pre-assembly of the tips 16 into the peg holes of the plate 10 is preferably performed so that surgeon does not have to thread the drill guide tips 16 with the plate once the plate 10 is positioned on the bone during the procedure. The pre-assembly can be done by the operating room technician or at the factory. In a preferred method of pre-assembly, a nest of short pins 24 is placed beneath the plate such that the pins extend through the holes in the plate along the same angles as the axes of the holes. The pins 24 then guide the tips to be thread into the holes at the correct angle. The pins 24 and insertion tool 18 are sized such that they do not interfere with each other. Alternatively, no nest is utilized and the tips 16 are individually guided into the holes at the appropriate angle. As shown, each drill guide tip 16, when discretely coupled to the bone plate 10, is assembled into its respective threaded hole, is completely decoupled from the other drill guide tips other than through the plate. The drill guide tips 16 may be reusable or disposable.

Figure 3:
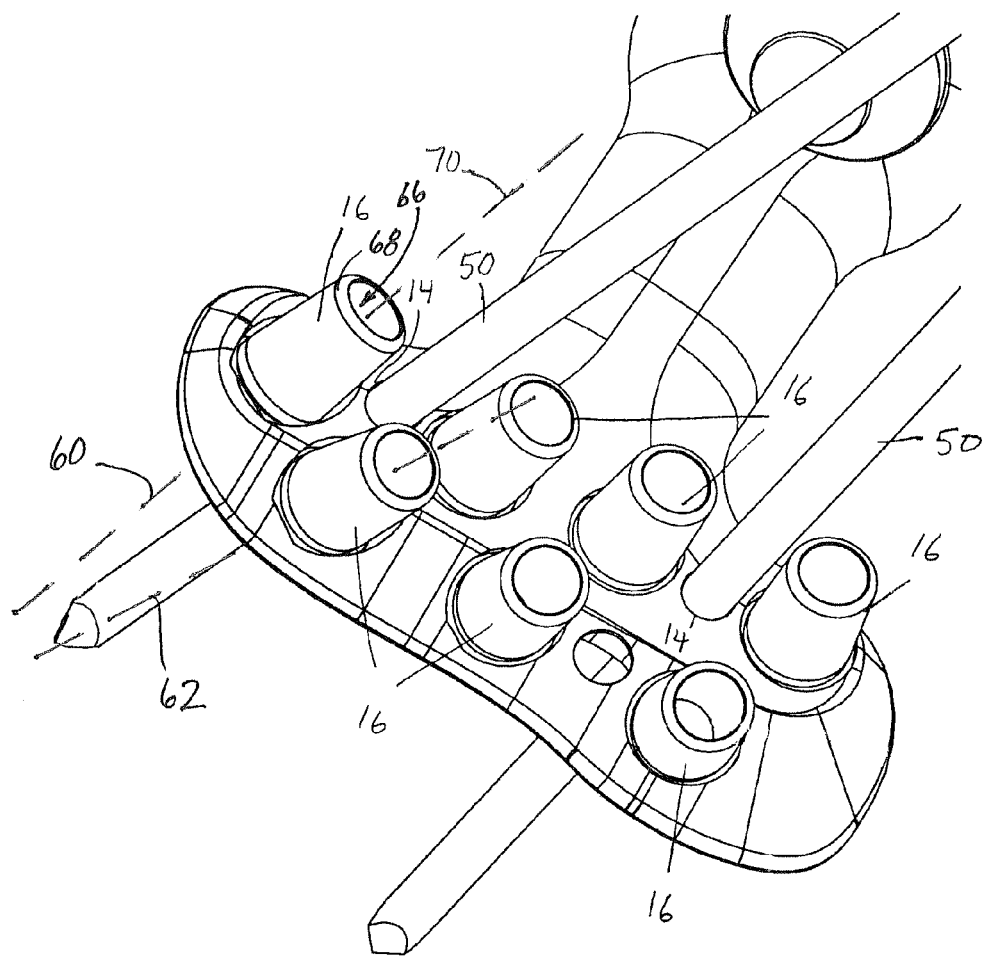
FIG. 3 is a perspective view of the bone plate loaded with drill guide tips and K-wires.
Figure 4:
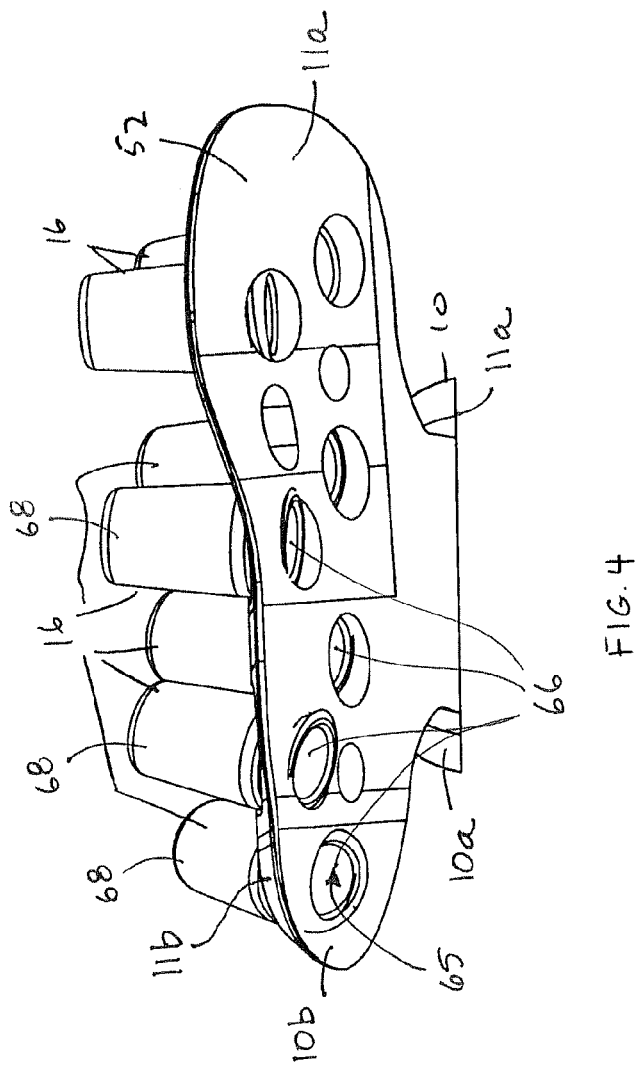
FIG. 4 is a front end view of a head portion of the plate showing that the drill guide tips do not protrude through the bottom surface of the plate.

Referring to FIGS. 2 and 3, the tips 16 preferably have a frustoconically tapered upper portion 30 and lower threaded portion 32, and are sufficiently short so that they do not interfere with adjacent tips, adjacent structure on the plate, or structure intended to be inserted through the plate, e.g., K-wires 50 through alignment holes 14. The threaded lower portion 32 is smaller in diameter than the lower end of the frustoconical upper portion 30. The lower threaded portion 32 of the tips do not have to be as long as conventional drill guides, as the threading into the plate is done away from the surgical environment under easier conditions, whether at the factory (best case) or pre-implantation at the medical facility. Shortening the threaded portion reduces protrusion of the guide tip below the plate relative to convention drill guides, allowing the plate 10 to sit closer to the bone while drilling, as discussed further below. Each drill guide tip 16 has an internal surface 65 defining a bore 66, a proximal guiding end 68, and a longitudinal axis 70 extending through a radial center of the bore 66, and particularly through the axis of the threaded lower portion 32. In this manner, when the drill guide tip 16 is connected to the plate 10 at a threaded hole 14, the longitudinal axis 70 is coaxial with the axis of the respective threaded hole 12 in which it is inserted as shown at FIG. 3.

The drill guide tips also eliminate the need to "countersink" holes for a drill guide for the distal row of holes in the plate. More particularly and for the following reasons, in the prior art it is initially necessary to drill holes in bone through the distal row of peg holes with a drill bit larger than the diameter of the peg shaft which will eventually be inserted through the peg holes. The plate is very thin at the distal row. The prior art drill guide has a "nose" section which is cylindrical and unthreaded and approximately 0.030" long, which is slightly longer than the pitch of the peg-hole thread (0.023"). The nose section diameter is just under the inner diameter of thread so that it guides itself with one full turn of the thread and establishes the direction of the hole before the threads are engaged. If the plate thread depth is very small (as is the case for distal holes) there is no room below the plate for the nose section of the drill guide because the bone block entry. Thus, countersink holes must be drilled.

In accord with the invention, the drill guide tips do not require a "nose" section since they will be assembled with some other guidance (e.g., the above described nest of pins 24) or freehand. The drill guide tips can be made very short since they need just to hold on to the threads of the peg holes. One and half threads of engagement has been shown to provide a satisfactory coupling of the tip to the plate, and referring to FIG. 4 provides that the drill guide tip 16 does not protrude through the bottom 52 of the plate 10. In addition to eliminating the requirement for countersinking, the fact that drill guide tips are so short results in the plate seating almost completely flush on the bone. Furthermore, the cylindrical unthreaded nose portion of the conventional drill guide, whose only job is to help the surgeon find by feel the current angle of the peg hole, is not required. A preferred size for each tip is preferably approximately 0.150-0.250 inch in length. As the drill guides tips are up to approximately 0.25 inch in length, and the plate is approximately 0.1 inch thick, the drill guide tips have a length that extends above the second surface 11b of the bone plate 10 by more than the thickness of the bone plate and which displaces the proximal guiding end 68 of the tips 16 from the second surface of the plate.

There are two options for using the tips. According to a first option, the tips 16 are used as the sole guide for a drill bit and then removed with a tool similar to the insertion tool 18. As shown at FIGS. 3 and 4, the drill guides used on the head portion 10b of the slate at an one time are all of a common size; i.e. diameter and length. The length of the tips provide provides sufficient guidance for the drill bit. Referring to FIGS. 1 and 2, it is seen that the length of a guide tip 30 is longer than the diameter of the circular opening 22 of the cylindrical bore 66 defined through upper and lower portions 30, 32. In this use, the inner surface 65 of the tip is preferably hard, e.g., metal. Thus, the tips 16 may be made entirely of metal or have an outer plastic body with an insert molded metal tube, e.g. hypotube, which is hard and readily available with thin walls.

Figure 5:
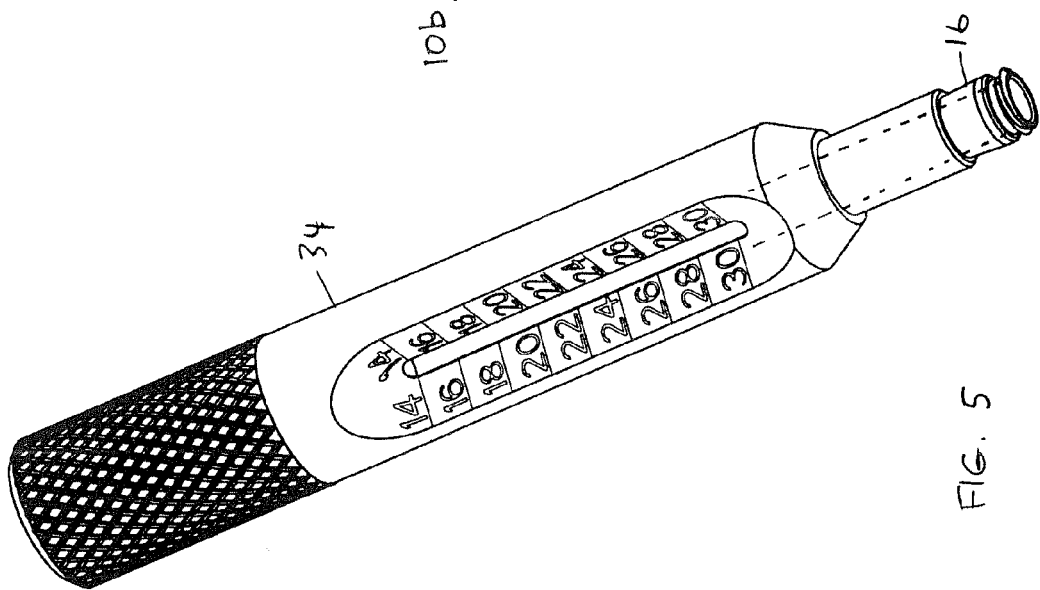
FIG. 5 is a perspective view of a drill guide tip and drill guide extension.

Referring to FIG. 5 and according to a second option, a drill guide extension 34 may be attached to the top of the tip 16. The tip 16 and extension 34 together function as a full length drill guide. The engagement between the drill guide extension 34 over the tip 16 is preferably such that a continuous constant diameter path is provided through the interiors of the extension and tip. To that end, the end 36 of the extension 34 is preferably stepped to fit the upper portion of the tip. The surgeon drills through the drill guide extension and tip, thereby taking advantage of the longer guidance which may be used in conjunction with a scale and/or gauge to measure the depth of the drilled hole for peg length selection. After drilling, the extension 34 and tip 16 are removed from the plate 10, and the extension 34 may also function as a tool for tip 16 removal. In fact, the taper at the upper portion 30 of the tip provides a means for axial and frictional engagement by the extension 34 which permits rotational engagement. Once removed from the plate, the tip is then is pulled of the extension by hand or may be dispensed into a container without manual contact.

It is desirable to have some provision within the surgical set to collect the tips for counting as they are removed; i.e., to ensure that all tips from the plate are removed from the surgical site. In order to facilitate collection of the tips, it is desirable that the drill guide tips have a very conspicuous color, e.g., green or blue. If made out of metal, it may be desirable to make them out titanium or aluminum and anodize them in a bright color that contrasts with the background in the surgical wound and the bone plate. A specialized container may be provided, or a dummy plate with threaded holes may be used to attach the tip thereto.

For drilling through the tips 16 where no drill guide extension is used, it may be desirable to modify the flutes of the drill bit, e.g. shortening and/or increasing twist, to reduce the play within the tip.

Other embodiments of the tips and extensions may be provided. For example, referring to FIGS. 6 and 7, the tips 116 may have an upper portion 130 with a exterior hex shape, or any non-circular exterior cross-sectional shape that will facilitate torque transmission. To remove the tip from the plate the surgeon rotates the extension, unthreading the tip.

Turning now to FIGS. 8 and 9, according to another embodiment of the invention, the tips 216 may be joined to the extension via one or more lateral protrusions 240 on the body 230 of the tip and corresponding "key slots" 242 in the extension 234.

Referring to FIG. 10, according to a further embodiment of the invention, the tips 316 may be joined to the extension by providing one or more corners 344 to the inner circular opening 322 of the tip, and one or more outer corresponding corners on the extension which frictionally engage in the tip.

Turning to FIGS. 11 and 12, according to another embodiment of the invention, the tips 416 may include an upper radially arranged slots 446 (e.g., 180° or 120° separation) and the extension 434 includes corresponding radially arranged pegs 448 which engage the tips 416 at the slots 46.

There have been described and illustrated herein several embodiments of a bone plate with pre-assembled drill guide tips and methods of using the same. While particular embodiments of the invention have been described, it is not intended that the invention be limited thereto, as it is intended that the invention be as broad in scope as the art will allow and that the specification be read likewise. Thus, while the tips have been shown with respect to a volar plate for dorsally displaced fractures, it will be appreciated that the tips may be used for threaded holes on other bone plates as well. In addition, while particular engagements between the tips and the insertion/removal tool and the tips and drill guide extension have been disclosed, it will be understood that other suitable engagements can also be used. Also, while the drill guide tips are described as threaded into the peg holes, it is appreciated that non-threaded assemblies which maintain the tips in alignment with the axes of the peg holes can also be used. It will therefore be appreciated by those skilled in the art that yet other modifications could be made to the provided invention without deviating from its spirit and scope as claimed.

What is claimed is:

1. A bone plate system for use with fasteners for fixation of a fractured bone, said system comprising:
   a) a bone plate for placement on the bone, said bone plate includes an elongate shaft for placement along the diaphysis of the bone, and a head angled out of plane relative to said shaft for placement at the metaphysis of the bone, said head of said bone plate defining a plurality of threaded first holes for receiving a plurality of the fasteners in engagement with said threaded first holes, said threaded first holes defining respective hole axes extending centrally through said first holes, said plate including a bone contacting first surface, an opposite second surface, and a thickness extending in a dimension between said first and second surfaces; and
   b) a plurality of tubular drill guide tips threadedly engageable within said plurality of threaded first holes of said bone plate in axial alignment with said respective hole axes, each drill guide tip discretely couplable to said plate without coupling to the other of said drill guide tips other than through said plate,
   each drill guide tip having an internal surface defining a bore, a proximal guiding end, an externally threaded distal end for engagement with said threaded holes, and a longitudinal axis extending through a radial center of said bore,
   each said drill guide tip having a body portion extending between said guiding end and said plate, said body portion having a length that extends above said second surface of said bone plate by more than said thickness of said bone plate, yet said length is sufficiently short so that said body portion does not interfere with a body portion of an adjacent drill guide tip,
   said body portion of said drill guide tip having a tapered portion that tapers to a reduced exterior diameter, and when said tapered threaded distal end of said drill guide tip is threadedly engaged within a respective one of said threaded first holes, said reduced exterior diameter of said body portion is located above said second surface of said plate.

2. A bone plate system according to claim 1, wherein: said tapered portion of said body portion is conically tapered.

3. A bone plate system according to claim 1, wherein: said internal surface of said proximal guide end of said drill guide tip defines recessed corners.

4. In a bone plate for use with fasteners for fixation of a fractured bone, the bone plate defining a plurality of threaded first holes for receiving a plurality of the fasteners in engagement with the threaded first holes, the threaded first holes defining respective holes axes extending centrally through the threaded first holes, the bone plate including a bone contacting first surface, an opposite second surface, and a thickness extending in a dimension between said first and second surfaces, the improvement comprising:

a plurality of tubular drill guide tips simultaneously threadedly engageable to said threaded holes of said bone plate in axial alignment with said fixed hole axes, each drill guide tip having an internal surface defining a bore, a proximal guiding end, an externally threaded distal end for engagement with said threaded holes, and a longitudinal axis extending through a radial center of said bore, said drill guide tip having a body portion extending between said guiding end and said plate, said body portion of each said drill guide tip includes a tapered portion that tapers in diameter, said drill guide tip has a length that extends above said second surface of said bone plate by more than said thickness of said bone plate, yet said length is sufficiently short so that said body portion of said drill guide tip does not interfere with a body portion of an adjacent drill guide tip.

5. The improvement of claim 4, wherein:
said drill guide tips are simultaneously threadedly engaged within respective threaded holes of said bone plate.

6. The improvement of claim 4, wherein:
each drill guide tip is of a common size.

7. The improvement of claim 4, wherein:
each drill guide tip is a common diameter.

8. The improvement of claim 4, wherein:
each drill guide tip is of a common length.

9. The improvement of claim 4, wherein:
each drill guide tip is discretely coupled to said plate, with complete decoupling from the other drill guide tips other than through said plate.

10. The improvement of claim 4, wherein:
said body portion of each said drill guide tip includes a tapered portion that tapers in diameter.

11. The improvement of claim 4, wherein:
said tapered portion tapers toward said proximal guiding end.

12. The improvement of claim 4, wherein:
said tapered portion is conically tapered.

13. The improvement of claim 4, wherein:
said internal surface at said proximal end of said drill guide tip defines a recessed structure allow a tool to apply a torque against said drill guide tip to effect rotational displacement of said threaded distal end of said drill guide tip relative to said threaded hole.

14. The improvement of claim 4, wherein:
said recessed structure includes a plurality of corners circumferentially displaced about said internal surface of said drill guide tip.

15. The improvement of claim 4, wherein:
said drill guide tip does not exceed 0.25 inch in length.

16. A bone plate system for use with fasteners for fixation of a fractured bone, said system comprising:
a) a bone plate for placement on the bone, said bone plate defining a plurality of threaded first holes for receiving a plurality of the fasteners in engagement with said threaded first holes, said threaded first holes defining respective hole axes extending centrally through said first holes, said bone plate includes a plurality a second holes for receiving a plurality of the fasteners therethrough, with said second holes being larger than said first holes, said plate including a bone contacting first surface, an opposite second surface, and a thickness extending in a dimension between said first and second surfaces; and
b) a plurality of tubular drill guide tips threadedly engageable within said plurality of threaded first holes of said bone plate in axial alignment with said respective hole axes, each drill guide tip discretely couplable to said plate without coupling to the other of said drill guide tips other than through said plate, each drill guide tip having an internal surface defining a bore, a proximal guiding end, an externally threaded distal end for engagement with said threaded holes, and a longitudinal axis extending through a radial center of said bore, each said drill guide tip having a body portion extending between said guiding end and said plate, said body portion having a length that extends above said second surface of said bone plate by more than said thickness of said bone plate, yet said length is sufficiently short so that said body portion does not interfere with a body portion of an adjacent drill guide tip, said body portion of said drill guide tip having a tapered portion that tapers to a reduced exterior diameter, and when said tapered threaded distal end of said drill guide tip is threadedly engaged within a respective one of said threaded first holes, said reduced exterior diameter of said body portion is located above said second surface of said plate.

17. A bone plate system for use with fasteners for fixation of a fractured bone, said system comprising:
a) a bone plate for placement on the bone, said bone plate defining a plurality of threaded first holes for receiving a plurality of the fasteners in engagement with said threaded first holes, said threaded first holes defining respective hole axes extending centrally through said first holes, said bone plate includes a plurality a second holes for receiving a plurality of the fasteners therethrough, and at least one of said second holes is non-threaded, said plate including a bone contacting first surface, an opposite second surface, and a thickness extending in a dimension between said first and second surfaces; and
b) a plurality of tubular drill guide tips threadedly engageable within said plurality of threaded first holes of said bone plate in axial alignment with said respective hole axes, each drill guide tip discretely couplable to said plate without coupling to the other of said drill guide tips other than through said plate, each drill guide tip having an internal surface defining a bore, a proximal guiding end, an externally threaded distal end for engagement with said threaded holes, and a longitudinal axis extending through a radial center of said bore, each said drill guide tip having a body portion extending between said guiding end and said plate, said body portion having a length that extends above said second surface of said bone plate by more than said thickness of said bone plate, yet said length is sufficiently short so that said body portion does not interfere with a body portion of an adjacent drill guide tip, said body portion of said drill guide tip having a tapered portion that tapers to a reduced exterior diameter, and when said tapered threaded distal end of said drill guide tip is threadedly engaged within a respective one of said threaded first holes, said reduced exterior diameter of said body portion is located above said second surface of said plate.

18. A bone plate system for use with fasteners for fixation of a fractured bone, said system comprising:
a) a bone plate for placement on the bone, said bone plate defining a plurality of at least three threaded first holes for receiving a plurality of the fasteners in engagement with said threaded first holes, said threaded first holes defining respective hole axes extending centrally through said first holes, said plate including a bone contacting first surface, an opposite second surface, and a thickness extending in a dimension between said first and second surfaces; and b) a plurality of tubular drill guide tips threadedly engageable within each of at least three of said threaded first holes of said bone plate in axial alignment with said respective hole axes, each drill guide tip discretely couplable to said plate without coupling to the other of said drill guide tips other than through said plate, each drill guide tip having an internal surface defining a bore, a proximal guiding end, an externally threaded distal end for engagement with said threaded holes, and a longitudinal axis extending through a radial center of said bore, each said drill guide tip having a body portion extending between said guiding end and said plate, said body portion having a length that extends above said second surface of said bone plate by more than said thickness of said bone plate, yet said length is sufficiently short so that said body portion does not interfere with a body portion of an adjacent drill guide tip, said body portion of said drill guide tip having a tapered portion that tapers to a reduced exterior diameter, and when said tapered threaded distal end of said drill guide tip is threadedly engaged within a respective one of said threaded first holes, said reduced exterior diameter of said body portion is located above said second surface of said plate.

19. A bone plate system for use with fasteners for fixation of a fractured bone, said system comprising:

a) a bone plate for placement on the bone, said bone plate defining a plurality of threaded first holes for receiving a plurality of the fasteners in engagement with said threaded first holes, said threaded first holes defining respective hole axes extending centrally through said first holes, said plate including a bone contacting first surface, an opposite second surface, and a thickness extending in a dimension between said first and second surfaces; and b) a plurality of tubular drill guide tips threadedly engageable within said plurality of threaded first holes of said bone plate in axial alignment with said respective hole axes, each drill guide tip discretely couplable to said plate without coupling to the other of said drill guide tips other than through said plate, each drill guide tip having an internal surface defining a bore, a proximal guiding end, an externally threaded distal end for engagement with said threaded holes, and a longitudinal axis extending through a radial center of said bore, each said drill guide tip having a body portion extending between said guiding end and said plate, said body portion having a length that extends above said second surface of said bone plate by more than said thickness of said bone plate, but does not exceed 0.25 inch and is sufficiently short so that said body portion does not interfere with a body portion of an adjacent drill guide tip, said body portion of said drill guide tip having a tapered portion that tapers to a reduced exterior diameter, and when said tapered threaded distal end of said drill guide tip is threadedly engaged within a respective one of said threaded first holes, said reduced exterior diameter of said body portion is located above said second surface of said plate.

20. A bone plate system for use with fasteners for fixation of a fractured bone, said system comprising:

a) a bone plate for placement on the bone, said bone plate defining a plurality of threaded first holes for receiving a plurality of the fasteners in engagement with said threaded first holes, said threaded first holes defining respective hole axes extending centrally through said first holes, said plate including a bone contacting first surface, an opposite second surface, and a thickness extending in a dimension between said first and second surfaces; and b) a plurality of tubular drill guide tips threadedly engageable within said plurality of threaded first holes of said bone plate in axial alignment with said respective hole axes, each drill guide tip discretely couplable to said plate without coupling to the other of said drill guide tips other than through said plate, each drill guide tip having an internal surface defining a bore, a proximal guiding end, an externally threaded distal end for engagement with said threaded holes, and a longitudinal axis extending through a radial center of said bore, each said drill guide tip having a body portion extending between said guiding end and said plate, said body portion having a length that extends above said second surface of said bone plate by more than said thickness of said bone plate, yet said length is sufficiently short so that said body portion does not interfere with a body portion of an adjacent drill guide tip, said body portion of said drill guide tip having a tapered portion that tapers to a reduced exterior diameter, and when said tapered threaded distal end of said drill guide tip is fully threadedly engaged within a respective one of said threaded first holes, said distal ends of said plurality of said drill guide tips do not protrude through said bone contacting first surface of said plate, and said reduced exterior diameter of said body portion is located above said second surface of said plate.

* * * * *